United States Patent [19]

Ginsberg et al.

[11] 4,276,258
[45] Jun. 30, 1981

[54] SAMPLE AND STAT FEEDING SYSTEM AND SAMPLE TRAY

[75] Inventors: Guenter Ginsberg, Miami; Bruce J. Hodgins, Hialeah, both of Fla.

[73] Assignee: Coulter Electronics, Inc., Hialeah, Fla.

[21] Appl. No.: 115,924

[22] Filed: Jan. 28, 1980

[51] Int. Cl.³ .................... G01N 1/14; G01N 35/06
[52] U.S. Cl. .............................. 422/64; 73/864.25; 364/497; 422/67
[58] Field of Search .................. 422/63, 64, 65, 67; 364/497, 498; 73/425.4 R, 425.6

[56] References Cited

U.S. PATENT DOCUMENTS

| | | | |
|---|---|---|---|
| 3,192,968 | 7/1965 | Baruch et al. | 422/64 X |
| 3,193,358 | 7/1965 | Baruch | 422/64 |
| 3,723,066 | 3/1973 | Moran | 422/64 |
| 3,764,268 | 10/1973 | Kosowsky et al. | 422/64 |
| 4,058,367 | 11/1977 | Gilford | 422/67 |
| 4,155,978 | 5/1979 | Naono et al. | 422/64 |

Primary Examiner—Ronald Serwin
Attorney, Agent, or Firm—Silverman, Cass & Singer

[57] ABSTRACT

A sample and stat feeding system for sequentially supplying a renewable supply of cuvettes with aliquots of sample liquids in a continuous processing mode. The sample liquids are contained in an annular sample tray having a plurality of sample vessels molded into the tray. The sample containers form two or more annular rows on the outer edge of the tray in which routine samples are maintained in an ordered sequence. Emergency samples (stats) and controls (standards) are maintained in separate auxiliary locations or arrays of locations which may be molded or separate cups placed in tray cavities. A sample pick up mechanism has a pick up probe which is rotated to define an arc across at least a substantial portion of the tray and at least one stat location. The tray is rotated to align the sample, stat and control cavities with the arc of the probe. Sample aliquots are picked up and dispensed into the cuvettes in a programed operation sequence, with each sample fluid being related to a particular patient and programed for one or more analytical tests such as measuring the chemical reaction resulting from the addition of one or more reagents from a reagent supply. The program sequencing includes inserting a control aliquot in some of the cuvettes at a predetermined frequency to monitor the accuracy of the machine. When a stat test occurs, the stat is inserted in the tray and the programed sequence is interrupted to load the stat into the reaction vessel. The order of sample locations is not disturbed since the stats and controls are maintained in separate locations. The sample tray preferably will be molded of inexpensive material so it may be thrown away after all sample aliquots have been loaded into respective cuvettes for testing.

20 Claims, 5 Drawing Figures

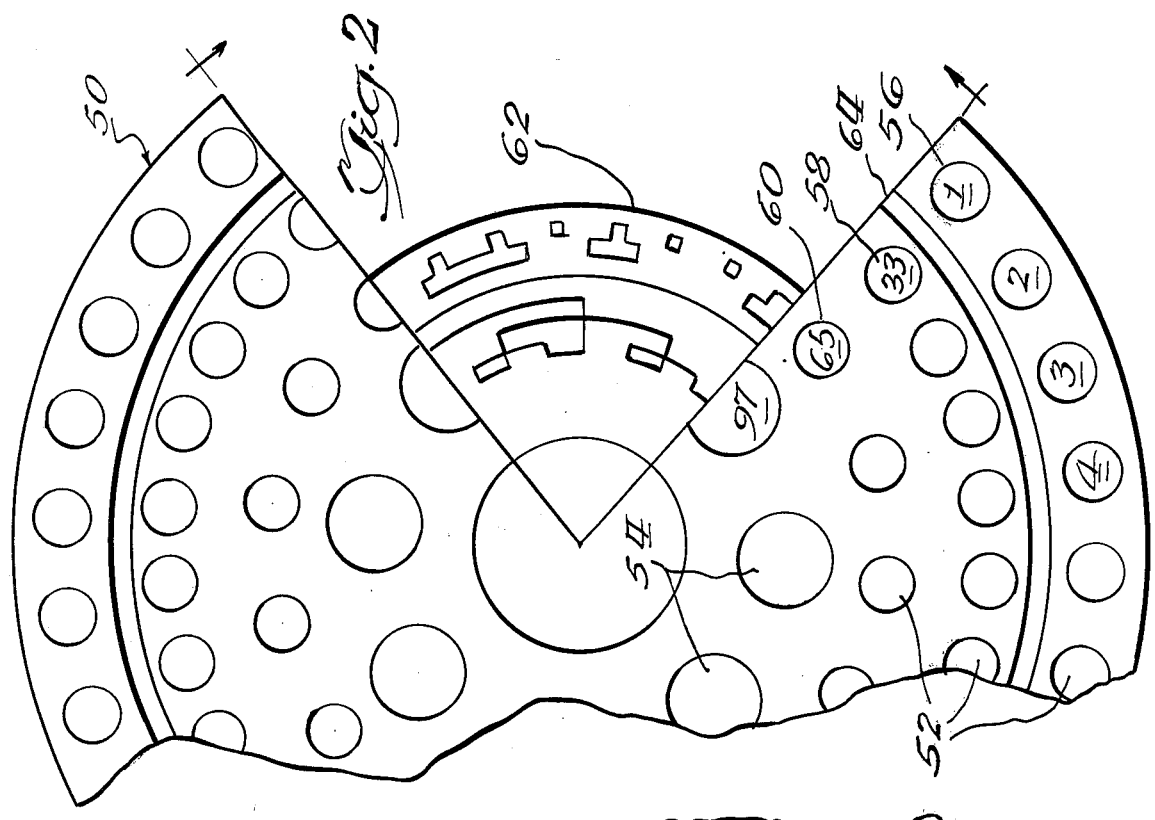
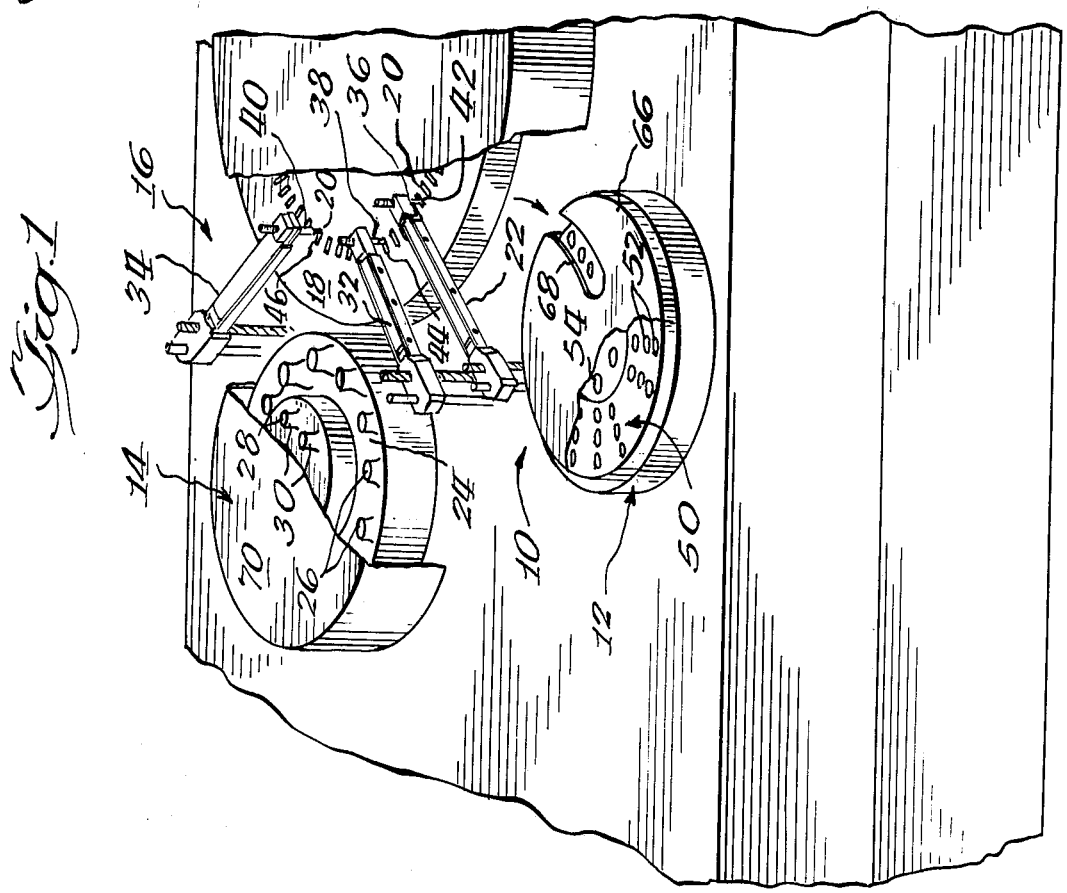

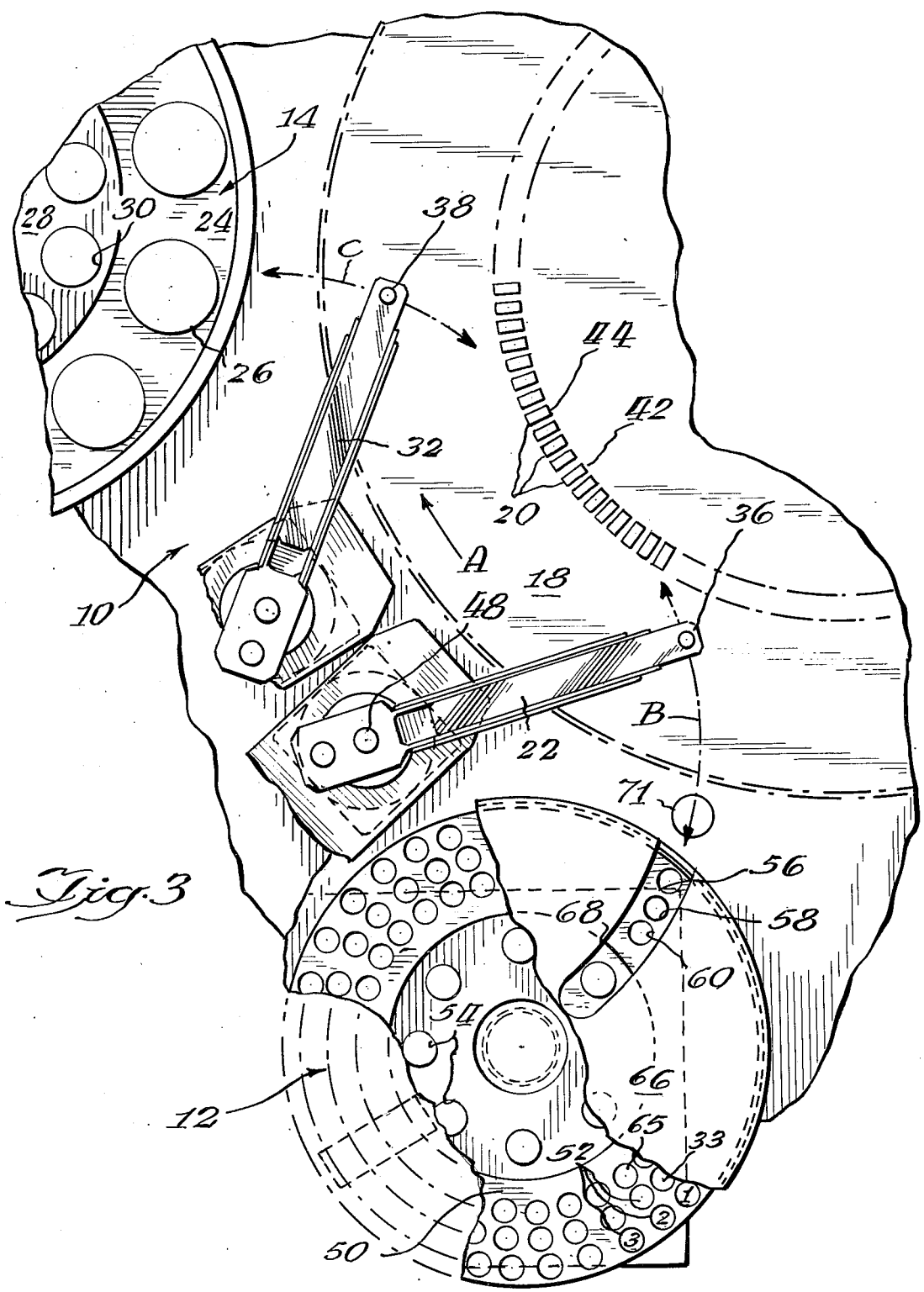

SAMPLE AND STAT FEEDING SYSTEM AND SAMPLE TRAY

CROSS REFERENCE TO RELATED APPLICATIONS

This invention is related to the subject matter disclosed in the following copending and commonly assigned applications which are incorporated herein by reference:

Apparatus For Monitoring Chemical Reactions and Employing Moving Photometer Means, G. Ginsberg et al, Ser. No. 846,337, filed Oct. 28, 1977, now allowed.

Cuvette Washing Apparatus, B. Hodgins, Ser. No. 115,692, filed Jan. 28, 1980, filed concurrently herewith.

System and Program for Chemical Reaction Observation with a Moving Photometer, G. Ginsberg et al, Ser. No. 115,734, filed Jan. 28, 1980, filed concurrently herewith.

Fluid Transfer Mechanism, V. Drbal et al, Ser. No. 115,691, filed Jan. 28, 1980, filed concurrently herewith.

Probe Washer, B. Hodgins, Ser. No. 115,625, filed Jan. 28, 1980, filed concurrently herewith.

Variable Stop Syringe, B. Hodgins et al, Ser. No. 115,624, filed Jan. 28, 1980, filed concurrently herewith.

BACKGROUND OF THE INVENTION

The invention relates to a system and method for sequentially supplying a plurality of cuvettes with aliquots of sample liquids in a continuous processing mode. More particularly, this invention concerns the supplying of samples and stats each of which may provide a single aliquot or plurality of aliquots which are subjected to chemical reactions with different reagents; which reactions are then analyzed.

The term "aliquot" was employed herein is a noun meaning a portion of a sample. The term "auxiliary sample" is used herein to encompass control or standard samples, emergency-type samples, and similar fluids in distinction from a normally sequenced arrangement from patient samples. The system supplies the aliquots to reaction vessels to which a reagent or reagents then may be added prior to testing of the aliquots. The testing may be performed by monitoring the absorbance of electro-magnetic radiation at a particular wavelength or wavelengths by the analyte.

One disadvantage of prior art analyzing systems is the inability easily to handle an emergency situation as it arises without destroying the total sequence of operations of the system. In such systems the samples are laid out in a predetermined order to be tested, such as 1 through 50 with the identification and position of each of the samples being fixed. If during the sequencing of the samples and the tests run on the samples an emergency situation or stat test is desired, a position is robbed of its sample. The emergency situation or stat test is a sample which must be analyzed immediately and thus the programed sequence of testing in progress must be interrupted. Each of these stat tests changes the programming of the tests and samples already in the programed test sequence in the analyzer. Each change in the predetermined order or programming of the tests and sample locations correctly must be entered and correlated so that the alteration of the sequencing is correctly noted in the system. This may result in the mismatching of a test and a sample resulting in an improper analysis related to a particular patient and all those following the mismatch in the sequence. It is extremely critical that a system accurately observe each sample reaction mixture being tested as well as have the flexibility to handle an emergency or stat situation should it arise during a sequence of testing without endangering the correct correlation of the test and samples already in the testing sequence.

A second problem encountered by the prior art devices is caused by dedicated reagent positions and typically a dedicated reagent dispensing mechanism for each position. In this case the array of cuvettes is segmented or divided into the number of positions required by the dedicated reagent positions. For example, 100 cuvette positions with 10 reagent positions results in samples from only 10 patients being tested without regard to the number of tests to be conducted on the sample from each patient. Patient No. 1 might require only one test, but all ten positions have to be alloted for that patient's sample in the device. Each of the nine empty positions may not be utilized so that the hundred position machine only is effective as a ten sample machine. If this problem is doubled by including ten second reagents, then the one hundred position machine would be divided in half again such that samples from only five patients could be analyzed at one time. This results in a great increase in elapsed time for a given throughput as well as a corresponding decrease in the efficiency of the operation.

SUMMARY OF THE INVENTION

The above and other disadvantages of prior art sample and stat feeding systems and techniques are overcome in accordance with the present invention by providing a single pick up position for each of a plurality of samples, stats, controls, first reagents and second reagents which are moved to respective pick up positions. A renewable supply of cuvettes sequentially is stepped or moved first to a dispensing position for the sample, stats and controls and then to one or more reagent dispensing positions. Each sample in the sample tray supplies one or more aliquots to the reaction vessels in a predetermined sequence interspersed with controls so that the operation of the machine accurately may be monitored for proper operation. The sample tray includes a separate stat position into which stats may be loaded and then the program sequence interrupted to insert one or more aliquots from the stat or stats into the renewable cuvette array before preceding to the next regular sample without destroying the location sequence of the samples.

BRIEF DESCRIPTION OF THE DRAWINGS

FIG. 1 is a partial perspective view of the sample and stat feeding apparatus of the invention;

FIG. 2 is a partial top plan view of the sample tray with a portion broken away to show the positioning code wheel of the tray;

FIG. 3 is a top plan view with parts broken away showing the operational relationships between the sample tray, reagent tray and cuvette array;

DESCRIPTION OF THE PREFERRED EMBODIMENTS

Figure 4:
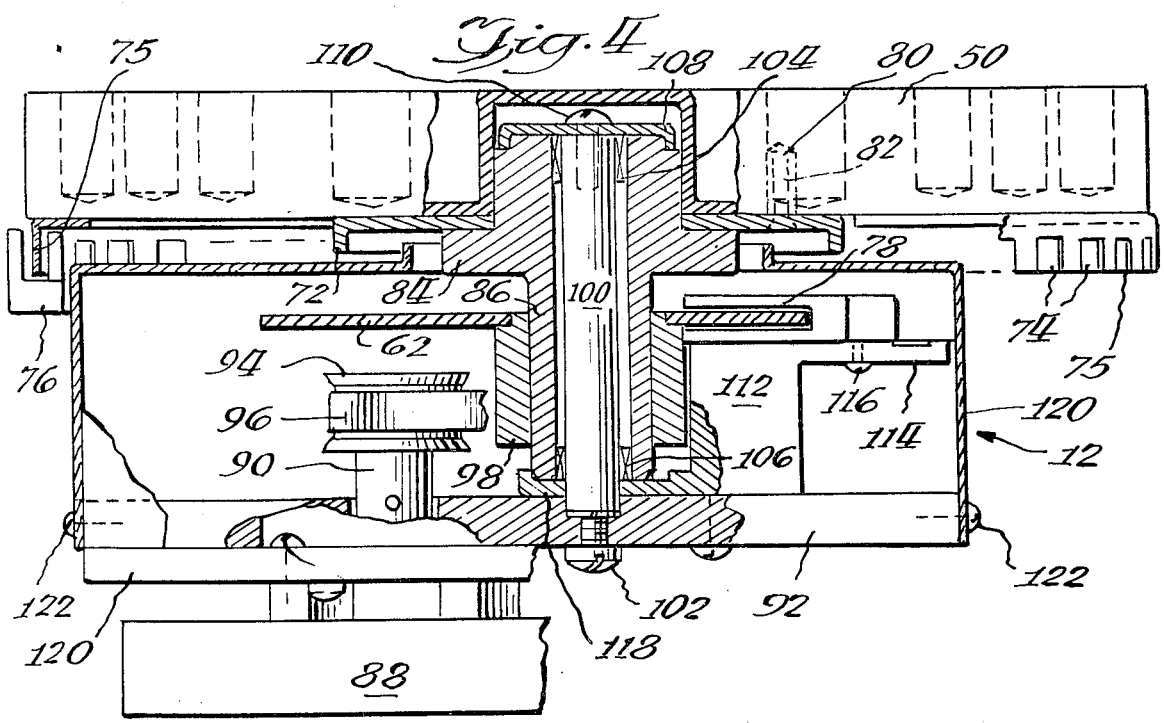
FIG. 4 is a side sectional view of one embodiment of the cuvette tray and its associated positioning mechanism.

Referring now to FIG. 1, an apparatus constructed in accordance with the invention is designated generally by the reference character 10. The major units of the sample and stat feeding system 10 include a sample supply 12 and a reagent supply 14. The samples from the supply 12 and the reagents from the reagent supply 14 are transferred to and observed in a chemical reaction analyzer 16. Any type of analyzer 16 may be utilized with the sample and stat feeding system 10 of the invention; however, for ease in describing the system 10 one particular analyzer 16 will be described.

The analyzer 16 includes a cuvette rotor 18 which includes a plurality of cuvettes or cuvette cavities 20 in which the sample aliquots are dispensed and mixed with reagent aliquots which are then analyzed by the analyzer 16. The sample supply 12 includes samples, stats and controls or blanks which are picked up from the sample supply, moved to and dispensed into the rotor cuvettes 20 by a sample dispensing arm 22. The reagent supply 14 typically will have a first reagent ring 24 containing a plurality of first reagents in separate containers 26 and a second reagent ring 28 containing a second plurality of reagents in second reagent containers 30. The first reagents are picked up from the first reagent ring 24, moved to and dispensed into the rotor cuvettes 20 by a first reagent dispensing arm 32. The second reagents are picked up from the second reagent ring 28, moved to and dispensed into the rotor cavities by a second reagent dispensing arm 34.

The cuvette rotor 18 is rotated or stepped to present an endless supply of cuvettes 20 into which the sample aliquots and reagents may be placed to be analyzed. The cuvette rotor is not essential and could be replaced by an endless chain or belt if desired. Referring to FIGS. 1 and 3, the picking up and dispensing of the samples, controls, stats and first reagents into the cuvettes 20 may most clearly be seen. The number of cuvettes is not critical, for example, there may be a hundred and twenty cuvettes spaced circumferentially, preferably equiangular around the rotor 18. The cuvettes 20 are light transmissive and the various reactions and other operations taking place therein may be monitored by one or more photometers (not shown). The photometers will include a beam of light which passes through the cuvettes 20 one at a time and the liquids therein (if any) following which the transmitted light is sensed by a photodetector. The light beam preferably is rotated relative to the disc 18 to sequentially scan each of the cuvettes 20 and its contents. The analyzer 16 then may measure the reaction in each vessel 20, either for a rate of reaction test or an end point condition or for both, if desired.

Referring first to the sample dispensing operation, the sample arm 22 is pivoted around an axis 48 and carries the pick up and dispensing probe 36 extending downwardly at its distal end. The movement of the probe 36 on the arm 22 describes an arc B when the arm 22 is rotated between the sample supply and the cuvettes 20. The specific structure of the arms, 22, 32 and 34 is not critical; however, each of the arms or their respective probes must have the capability of being pivoted upon an axis and raised and lowered to pick up and dispense the fluid quantities. The associated valving and conduits is not shown, but would be readily provided by conventional techniques.

Each of the arms 22, 32 and 34 is shown lowered with the respective probes in the dispensing position in a respective cuvette 20 in FIG. 1. As shown in FIGS. 2 and 3, the main element of the supply 12 is a sample disc or tray 50. The sample tray 50 includes at least two arrays of fluid cavities 52 and 54. The first array of cavities 52 includes at least two concentric rows of cavities 56 and 58. In the specific embodiment shown, a third row 60 is also included in the array 52 which may contain samples or controls. The array of cavities 54 may include one or more rows of cavities, only one of which is shown in this specific example.

Further, although the size of the cavities 52 and 54 is not critical, the cavities 54 will typically be larger than the cavities 52 and may be large enough for separate containers of stats or blanks and controls to be placed therein. If row 60 is utilized for the blanks and controls the cavities therein preferably would be larger than those in rows 56 and 58. All the cavities preferably will be molded into the tray 50. As shown in FIG. 2, the tray 50 has associated with it a code wheel 62 which allows the precise positioning of the sample tray in the supply 12. The code wheel has any conventional type of binary coding, which may be metallic strips or holes through the code wheel or disc 62 which may be read by an optical reader (FIG. 4).

Each of the cavities will be filled with a particular sample fluid related to a particular patient for the cavities 52 and the cavities 54 may include the controls and blanks or may be empty awaiting a stat or emergency situation. The tray 50 is positioned in the supply 12 so that each of the cavities 52 and 54 has a specific location indicated by the code wheel 62. The individual samples are identified by position when they are loaded into the tray 50 and the identity and location is programmed into the analyzer 16 or system 10 so that the identity of the sample aliquot loaded into each cuvette 20 and the tests for each aliquot are maintained in sequence. Each of the samples located in the cavities 52 may have one or more aliquots placed in one or more of the cuvettes 20 for different reagents to be added to for different tests to be run on the fluid. The tray 52 may include one or more troughs or cavities 64 which will hold fluid, such as water, to maintain the humidity under a cover 66 to keep the sample, stats and controls from evaporating while they are being loaded into the cuvettes. Cover 66 preferably will have a slot 68 which has an arcuate opening, the center of which is aligned with the arc B to allow the sample probe to pass through the cover to the respective cavities in the rows 56, 58, 60 or the array 54. Thus the desired one of the cavities 52 or 54 is rotated to the slot 68 prior to being picked up by the arm 22, which then transfers the aliquot from the cavity to the cuvette 20 for analyzing.

Once the sample aliquot has been placed in the cuvette 20 it is moved by the rotor 18 to the first reagent dispensing position 44. At that position the arm 32 will operate in a manner similar to the dispensing arm 22 and will rotate to a reagent cavity or bottle 26 containing the specified reagent for that aliquot in the first reagent ring 24. The reagent supply 14 also will include a cover 70 to prevent the reagents from evaporating. The reagent cover 70 also may have a slot (not shown) similar to the sample cover slot 68 or it may only have a small hole since each of the containers or cavities 26 in the ring 24 will be concentric with the center of rotation of the ring 24. Not all sample aliquots will of course receive a first reagent at the first reagent dispensing location 44 and some may receive only the second reagent in a similar manner from the second reagent dispensing arm 34 at the second reagent dispensing position 46. In some cases the sample aliquot may receive a second reagent at location 46 in addition to the first reagent at location 44 for the particular reaction to be analyzed. The second reagent ring 28 also has a hole in the cover 70 (not shown).

Figure 5:
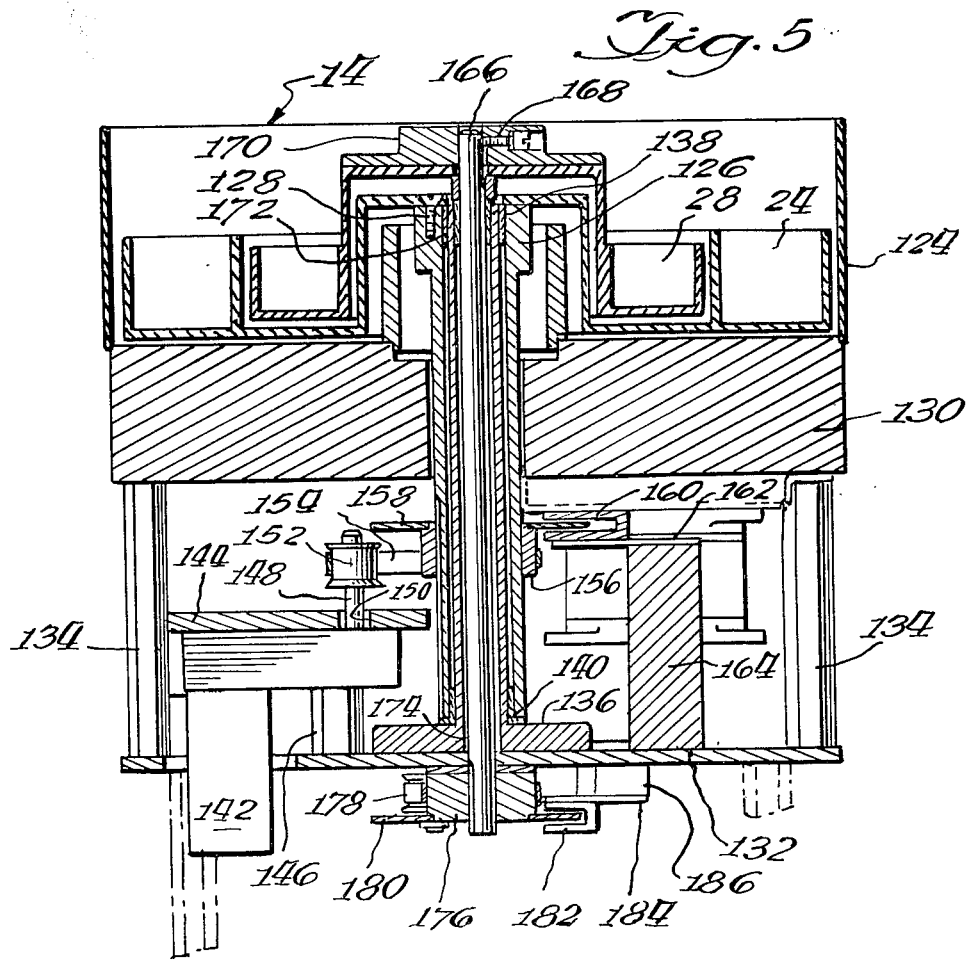
FIG. 5 is a side sectional view of the reagent trays and their respective positioning mechanisms.

To describe the operation of the system 10, the operations or one aliquot of sample fluid from cavity 2 will be described. Each of the fluids and their respective cavities is precisely located with the code wheel 62 and associated drive mechanisms (FIGS. 4 and 5). Assuming for instance that there are thirty-two cavities in each of rows 56 and 58, then cavities 1 through 32 will be in row 56 while cavities 33 through 64 will be in row 58. In the embodiment shown in FIG. 3, cavities 65 through 96 will be in row 60, while a lesser number will be in the tray 50 of FIG. 2. The center of each of the cavities 1, 33, 65 and 97 (FIG. 2) are aligned such that when the tray 50 is rotated to align one of them with the slot 68, each of them will be aligned on the arc B.

Following the picking up of the sample aliquot prior to the first aliquot from cavity 2, the tray 52 will be rotated to align the cavity 2 with the slot 68. After the prior aliquot is dispensed in location 42, the rotor will move the next empty cuvette into position at location 42. At the same time, the arm 22 will be rotated to position the probe 36 above the cavity 2 in the slot 68. The probe 36 will be moved down into the fluid in cavity 2 pick up the sample aliquot, be moved up and be rotated to location 42. The probe 36 then will be moved down into the cuvette 20, dispense the aliquot and be removed from the cuvette 20. While the sample aliquot is being dispensed, the first and second reagent probes 38 also may be dispensing reagents in respective cuvettes in locations 44 and 46.

Assuming that the first aliquot from cavity 2 is programmed for a test utilizing a reagent from the first reagent ring 24, the reagent will be added when the cuvette has been moved to the location 44. Again, after dispensing the reagent into the prior aliquot (if any) the reagent ring 24 will be rotated to position the programmed reagent into position aligned with an arc C defined by the rotation of the probe 38 on the arm 32. The probe 38 will pick up the reagent aliquot and move and dispense it into the first aliquot in the cuvette now at location 44. In a like manner, a second reagent may be added to the first aliquot at location 46. The location of the dispensing positions is not critical and the dispensing arms could be placed on opposite sides of the respective sample and reagent supplies if desired.

Control aliquots may be added to the cuvettes 20 at location 42 at a predetermined frequency, such as every tenth cuvette to check the operation and accuracy of the analyzer 16. The system 10 and the analyzer 16 will operate to pick up the control from the specified cavity in the array 54 or row 60 as required, and then will reposition the tray 50 so the second aliquot may be picked up from the cavity 2.

If a stat test is desired, for example, before the third aliquot from the cavity 2; then the stat fluid will be placed into a specified empty location in the array 54, such as cavity 97. The tray 50 then is rotated, after the second aliquot is picked up, to align cavity 97 with the slot 68 and arc B. The stat may be placed in the cavity 97 itself or may be in a separate container placed in the cavity 97. The probe 36 then will pick up and dispense the stat fluid in an identical manner to any other sample fluid. The tray 50 is then repositioned with cavity 2 again aligned in the slot 68. Thus, the flexibility of the system 10 is greatly enhanced by having the separate control and stat locations while maintaining accuracy of the sample fluid locations, because they are not disturbed for either a control or stat operation. The stats also may be placed in any other location on the arc B such as a separate non-movable cavity 71. The location 71 would permit the tray 50 to remain in position for the pick up of the next sequential aliquot, eliminating two movements of the tray 50.

Referring now to FIG. 4, the drive mechanism and locating mechanism for the sample supply 12 is best illustrated. The sample tray 50 preferably is a throw away tray which is mounted on a mounting disc 72. The tray preferably is a throw away tray, because the next tray can be prepared while the first tray is being operated on in the sample and stat feeding system 10 as described above. The tray 50 may be monitored by the sample and stat feeding system 10 and may have a series of punch out tabs 74 depending from a bottom rim 75 of the tray 50. These tabs may be removed when the tray is filled with samples so that the identification of each tray in the system 10 is assured. When the tray 50 is loaded into the sample and stat feeding system 10 on the mounting plate 72, it will be rotated and the tabs read by a reader 76 to identify the tray and the location of each of the samples, stats and blanks in the cavities 52 and 54 to assure the proper tests are taken on the samples and the results matched with the proper samples. The alignment with the slot 68 is controlled by the analyzer 16 or the feeding system 10 utilizing the code wheel 62 which rotates with the mounting plate and is read by an optical reader 78. Each of the trays 50 will include an aperture 80 opening through the bottom thereof into which will fit a locating pin 82 mounted in the mounting disc 72. Thus, the position of the tray 50 on the disc 72 is assured and the position of the tray 50 with respect to the pick up slot 68 then is controlled with the code wheel 62 and reader 78.

The mounting disc 72 is mounted on an outwardly extending flange 84 of a drive shaft 86. The drive shaft 86 is rotated by a motor 88 through a drive shaft 90. The motor is mounted to the bottom of a base plate 92 of the supply by a plurality of pins 93. The distal end of the shaft 90 carries a drive belt 96 which is engaged around the drive pulley 94 and a pulley 98 which is mounted on the drive shaft 86. The code wheel 62 may be mounted on the upper end of the pulley 98.

A non rotating main shaft 100 is mounted to the base plate 92 by a screw or other mounting means 102. The drive shaft 86 is spaced from the main shaft by an upper and lower bearing 104 and 106 and rotates around the main shaft 100. The shaft 100 includes a cover plate 108 which is affixed to the shaft by a screw 110. The cover plate prevents foreign matter from interfering with the bearings 104 and 106. The code wheel reader 78 is mounted on a block 112 on an outwardly extending flange 114 thereof. The reader 78 may be mounted to the flange 114 by a screw 116 extending therethrough into the reader 78. The reader block 112 includes a lower flange 118 which extends to and passes around the shaft 110 to form a thrust bearing for the drive shaft 86. The mounting of the block by the flange 118 around the shaft 100 also precisely locates the reader 78 with respect to the code wheel 62.

The drive assembly of the supply 12 preferably includes a cover member 120 to prevent foreign material from entering the drive assembly area and interfering with the code wheel 62 and reader 78 or other drive members of the supply assembly. The cover 120 may be mounted to the base member 92 by a plurality of screws 122. Although only a single drive is shown for the sample tray 50, the sample tray could be divided into one or more rings with the samples preferably in the outer rings 56 and 58, the controls in row 60 and the cavities 54 being reserved for stat or microstat (pre-mixed stats) cups. The rows 56 and 58 could be one separate tray and the rows 60 and the array 54 could be a separate tray. The number and size of the cavities is not critical and may vary depending upon the number of samples which are desired to be retained in a single loaded tray. For two separate sample rings the drive mechanism would be similar to the drive of the two reagents rings, as will be described next.

Referring now to FIG. 5, the details of the reagent supply may best be seen. The first and second reagent rings 24 and 28 are separately controlled and driven for greater flexibility, since they each supply different arms 32 and 34. It would be possible for the reagents to be in unitary tray, such as that shown for the samples 50 with a single drive, for use in a system having only one reagent dispensing arm. Referring to FIG. 3, this modification could be made by moving the reagent arm 32 farther toward the reagent supply or extending the length of the arm so that the arm would reach across the cuvettes 20 to have a dispensing position beyond point 44 and then return to the cuvette row on an arc for the first dispensing position 44. Alternately, both reagents could be dispensed in the same dispensing location which would require time for both reagents to be picked up and dispensed with the cuvette 20 in the position 44 on the rotor 18.

The two reagent rings 24 and 28 may have separate reagent containers placed into the respective cavities, such as shown in FIG. 1 or the reagents could be placed directly into the cavities if desired, in the same manner as the samples. Again as shown in FIG. 1, the cover 70 normally would cover the reagent supply to eliminate excessive evaportion or contamination of the reagents and to maintain the temperature of the reagents. The top portion of the cover is broken away with only a side wall 124 surrounding the periphery of the reagent rings 24 and 28 being shown in FIG. 5. The reagents preferably are kept at a substantially uniform temperature, generally chilled, such that the rings 24 and 28 preferably will be made from heat conductive metal which may be machined or cast.

The first reagent tray 24 is mounted to a rotating shaft 126 by a screw 128. The reagent supply 14 includes a base member 130 and a second lower mounting base 132 mounted to the base 130 by a plurality of pins 134. The pins 134 also may be enclosed by a cover (not shown) such as the cover 120. The shaft 126 is rotated about a stationary shaft 136 which is mounted to the base plate 134. The shaft 126 is spaced from the shaft 136 by an upper bearing 138 and a lower thrust bearing 140. The ring 24 and shaft 126 are rotated by a motor 142 mounted on a base 144 which is mounted to the base plate 132 by a plurality of pins 146. The motor 142 includes a drive shaft 148 which extends through an opening 150 in the base 144. The motor shaft 148 includes a pulley 152 mounted on its distal end. A drive belt 154 is mounted on the pulley 152 and about a pulley 156 mounted to the shaft 126. The position of the ring 24 with respect to its dispensing position on the arc C is controlled by a code wheel 158 read by a optical reader 160. The optical reader is mounted on a mounting plate 162 extending from a mounting block 164 mounted to the base plate 132.

The second inner reagent ring 28 is mounted on a central shaft 166 by a set screw 168 and a mounting block 170. The shaft 166 is spaced from and revolves inside the fixed shaft 136 by upper and lower bearings 172 and 174. The lower end of the shaft 166 extends through the base plate 132 and has a drive pulley 176 affixed to its lower end. The drive pulley 176 is driven by a belt 178 which is driven by a motor (not shown) similar to the motor 142. The drive pulley 176 includes a code wheel 180 similar to the code wheels 158 and 62 to position the ring 28. The code wheel 180 is read by an optical reader 182 mounted on an adjustable plate 184 mounted on a mounting block 186 which is mounted to the base plate 132. The base member 130 may include a heat sink to provide the appropriate cooling for the reagent rings 24 and 28.

Referring again to FIGS. 1 and 2, the tray 50 may be molded or machined from any material which will not react with the fluids placed therein. One convenient material is plastic. In utilizing the system 10 or tray 50 in an analyzer 16 which utilizes small amounts of fluid and for accuracy in the system it may be desirable to eliminate as much fluid carryover by the probes 36, 38 and 40 as possible. One method is to utilize level sensing with the probes 36, 38 and 40 so that they are not immersed in the fluids, but only contact the surface thereof. One method of level sensing, utilizes metallic probes 36, 38 and 40 or metallic elements, such as stainless steel which provides one side of a capacitive level senser. The path is completed through the fluid and container itself. This is not a problem with the reagents since the rings 26 and 28 are metal; however, a plastic tray 50 will not provide an electrical path. Therefor it is necessary to make the tray 50 conductive, but it still must be non-reactive with the fluids. One option is to mold graphite into the plastic tray 50, which is electrically conductive but non-reactive. A second option is to paint the area surrounding the cavities with metallic paint. A third option is to provide the molded cavities with a space around each cavity to which a metal ring or perforated plate may be mounted.

Many modifications and variations of the present invention are possible in light of the above teachings. The second reagents dispensed at the location 46, preferably should be those which do not need as much reaction and observation time as those dispensed at the position 44. The second reagents may be added in combination with the first reagents or the first and second reagents may be added to separate sample aliquots to form separate reagent mixtures. The situation also may arise where the number of reagent positions in the first reagent ring 24 are insufficient for a particular reagent volume, in which case the second reagent ring 28 would contain additional containers of the same reagent. This situation would arise where numerous tests are programmed to utilize the same reagent. It is, therefore, to be understood that within the scope of the appended claims, the invention may be practiced otherwise than as specifically described.

What is claimed and desired to be secured by Letters Patent of the United States is:

1. A feeding system for multiple discrete fluid samples comprising:
   A. at least one reaction vessel;
   B. a first tray assembly including a plurality of sequenced sample locations arranged in a first array, for containing liquid samples;
   C. at least one auxiliary sample location for containing auxiliary sample liquid, said auxiliary location positioned separate from said first array of sample locations;
   D. means for moving at least one of said sequenced and said auxiliary sample locations to a sample pick up station;
   E. means for picking up and dispensing an aliquot of liquid positioned at said sample pick up station;
   F. positioning means for moving said pick up and dispensing means to said sample pick up station and for then moving said aliquot to said reaction vessel to dispense said aliquot therein;
   G. a plurality of reagent locations arranged in a second tray assembly;
   H. means for moving one of said reagent locations to a reagent pick up station;
   I. means for picking up and dispensing a reagent aliquot positioned at said reagent pick up station and
   J. reagent positioning means for moving said reagent pick up means to said reagent pick up station to pick up said reagent aliquot and then moving said reagent pick up means to said reaction vessel to dispense said aliquot therein.

2. A system as claimed in claim 1, wherein:
said sequenced sample locations include cavities formed within said first tray; and
said auxiliary sample location including means for receiving a separate container for auxiliary sample.

3. A system as claimed in claim 2 wherein:
said cavities are molded in said first tray, each said cavity having an opening with a width less than the depth of said cavity.

4. A system as claimed in claim 1 wherein:
said first array of sample locations is arranged in at least two annular rings of locations located one within the other.

5. A system as claimed in claim 4 wherein:
said auxiliary sample location has a center located substantially on an arc having a center point located outside said first tray, said arc passing through substantially the center of one sample location on each of said rings.

6. A system as claimed in claim 4, 5 or 1 wherein:
said auxiliary sample location is substantially surrounded by said first array of sample locations.

7. A system as claimed in claim 4, 5 or 1 wherein:
a plurality of said auxiliary sample locations are formed in an annular array within said tray substantially surrounded by said first sample array.

8. A sample and stat supply as claimed in claim 1 further including:
orientation means for fixing the location of said sequenced and auxiliary sample locations.

9. A system as claimed in claim 1 wherein:
said first tray includes identification means adapted to be modified in use to separately identify said tray from other substantially identical trays.

10. A system as claimed in claim 1 wherein:
said first tray includes means for making said tray electrically conductive.

11. A system as claimed in claim 10 wherein:
said conductive means include said tray being molded from electrically conductive material.

12. A system as claimed in claim 11 wherein:
said electrically conductive material is graphite filled plastic.

13. A system as claimed in claim 1 wherein:
said auxiliary sample location and said first sample array are formed in said first tray assembly being rotatable to said pick up stations.

14. A system as claimed in claim 1 or 13 further including:
a plurality of auxiliary sample locations arranged in a second array;
means for moving a predetermind one of said second array locations to an auxiliary sample pick up location; and
said positioning means moving to said auxiliary sample pick up station to pick up an aliquot of auxiliary sample.

15. A system as claimed in claim 1 further including:
a plurality of reaction vessels, and driving means for moving each of said vessels sequentially into said dispensing position to receive said aliquots.

16. The system as claimed in claim 1 wherein said second tray assembly includes at least first and second annular structures carrying said reagent locations, and wherein said first and second annular structures are independently rotatable.

17. The system as claimed in claim 16 wherein said annular structures are concentric.

18. The system as claimed in claim 16 or 17 wherein at least one of said annular structures includes a code wheel means rotatably coupled to said annular structure for identification of said reagent locations.

19. The system as claimed in claim 1 or claim 15, further comprising:
second means for picking up and dispensing a reagent aliquot from said second tray assembly, and second reagent positioning means for moving said second reagent pick up means from said second tray assembly to a reaction vessel spaced from said second tray assembly, to dispense said aliquot into said reaction vessel.

20. The system as claimed in claim 19 wherein said first reagent positioning means and said second reagent positioning means are capable of moving said first pick up and dispensing means and said second pick up and dispensing means, respectively, to dispense said aliquots into the same reaction vessel while said reaction vessel is held stationary at a position spaced from both said first and second tray assemblies.

* * * * *